United States Patent [19]

Lynn

[11] Patent Number: 5,167,656
[45] Date of Patent: Dec. 1, 1992

[54] BLOOD CONTAINER HAVING LAY-FLAT SAMPLE RESERVOIR

[75] Inventor: Daniel R. Lynn, Lake Villa, Ill.

[73] Assignee: Baxter International Inc., Deerfield, Ill.

[21] Appl. No.: 644,177

[22] Filed: Jan. 22, 1991

[51] Int. Cl.⁵ .............................................. A61B 19/00
[52] U.S. Cl. ..................................... 604/409; 128/767;
73/863.71; 73/863.86; 137/255
[58] Field of Search ............................... 604/403–410,
604/256, 257; 128/764, 767; 73/863.71, 863.86;
157/255

[56] References Cited

U.S. PATENT DOCUMENTS

| | | |
|---|---|---|
| Re. 25,129 | 2/1962 | Walter . |
| 274,447 | 3/1883 | Kennish . |
| 2,777,443 | 1/1957 | Thomas et al. . |
| 2,834,345 | 5/1958 | Tabbert . |
| 2,950,716 | 8/1960 | Bellamy et al. .................. 604/409 |
| 3,064,647 | 11/1962 | Earl . |
| 3,110,308 | 11/1963 | Bellamy, Jr. . |
| 3,196,872 | 7/1965 | Katz . |
| 3,327,709 | 6/1967 | Nehring et al. .................. 604/409 |
| 3,463,357 | 8/1969 | MacLean, Jr. et al. . |
| 3,467,095 | 9/1969 | Ross ..................................... 604/408 |
| 3,654,924 | 4/1972 | Wilson et al. ..................... 604/409 |
| 3,870,042 | 3/1975 | Viguier .............................. 604/410 |
| 3,874,384 | 4/1975 | Deindoerfer et al. ............ 604/408 |
| 4,056,101 | 11/1977 | Geissler et al. . |
| 4,253,458 | 3/1981 | Bacehowski et al. . |
| 4,278,084 | 7/1981 | Pope, Jr. ............................ 604/406 |
| 4,453,940 | 6/1984 | Aoyagi et al. .................... 604/408 |
| 4,482,585 | 11/1984 | Ohodaira et al. . |
| 4,786,286 | 11/1988 | Cerny et al. ...................... 604/403 |
| 4,820,297 | 4/1989 | Kaufman et al. . |

FOREIGN PATENT DOCUMENTS 698308 6/1963 Italy .

Primary Examiner—C. Fred Rosenbaum
Assistant Examiner—Chalin Smith
Attorney, Agent, or Firm—Bradford R. L. Price; Garrettson Ellis

[57] ABSTRACT

The method is provided of collecting blood with a donor needle inserted into the vein, which comprises an improvement of: after drawing a desired amount of blood into the blood storage container connected to one end of flexible tubing, occluding flow through said flexible tubing at a point adjacent a flexible, transversely enlarged tubing portion positioned at a location on the tubing spaced from the ends. The flow occluding point is located between the enlarged tubing portion and the container, and the tubing portion is initially of lay-flat type, prior to passing blood through it. One then draws more blood through the needle to enter and fill the enlarged tubing portion. One then occludes flexible tubing between the enlarged tubing portion and the needle prior to withdrawing the needle from the vein of the blood donor.

10 Claims, 1 Drawing Sheet

BLOOD CONTAINER HAVING LAY-FLAT SAMPLE RESERVOIR

BACKGROUND OF THE INVENTION

In the science of blood collection for therapeutic purposes, blood is presently collected by inserting a donor needle into the vein of a donor. The donor needle communicates with a flexible, collapsible blood collection container through flexible tubing, which is connected at respective ends to the needle and the container.

The commercially available blood containers utilize a relatively long, flexible tubing connecting between the collapsible blood container and the donor needle, so that a series of segments may be formed by transverse sealing into the tubing after collection of blood plus filling of the donor tubing, so that the transverse, sealed segments in the donor tubing may be separately cut away for individual blood typing, cross-matching, and disease detecting procedures.

However, recently, because of the increase in number of potential diseases and the like for which donated blood is desirably tested, the users of blood containers, after the removing of the donor needle from the patient, are obtaining larger volumes of blood for sampling, typically by then sequentially inserting the donor needle into several evacuated vials to draw blood back out of the donor tubing into the vials. As this takes place, blood from the collapsible blood container is drawn back into the donor tubing.

Concern has arisen that the blood which has originally passed into the collapsible blood storage container is not suitable for certain forms of analytical testing of blood samples, because of the "dilution" effect provided by the liquid anticoagulant/nutrient which is initially present in the blood container into which the donated blood flows. Such anticoagulants such as CPD or ACD are believed to interfere with the accuracy of certain tests in some circumstances, for example, testing for antiHBc and for HTLV III.

Thus, there is a need for an increased supply of donated blood which has not been mixed with a liquid anticoagulant/nutrient normally found in blood storage containers, this supply being more than the volume which is typically carried in the volume of a length of donor tubing. At the same time, it is desirable for the blood collection container to optionally be capable of not collecting a significantly increased supply of blood over that normally found in the donor tubing, in those circumstances where augmented testing is not required, but only conventional testing as has been typically done in years past. In that circumstance, it of course would be desirable that an extra 20–30 ml. or so of unnecessary, collected blood should not be lost to the patient. Such unnecessary, collected blood also would present a disposal problem.

By this invention, a method is provided in which blood may be collected, with an increased volume portion of the blood collected being intended for sampling and testing, and being kept free of dilution with an anticoagulant/nutrient that is provided to stored blood. The method of this invention is compatible with a blood system in which an extra volume of such blood for sampling and testing does not have to be collected, but can be left with the patient.

DESCRIPTION OF THE INVENTION

The invention relates to a method including the step of connecting a donor needle into the vein of a blood donor. The donor needle communicates with a flexible, collapsible blood collection container through flexible tubing which is connected at its respective ends to the needle and container. One then draws blood through the needle and tubing into the container.

In accordance with this invention, after drawing a desired amount of blood into the container, one occludes flow through the flexible tubing at a point which is adjacent a flexible, transversely enlarged tubing portion positioned at a location on the tubing spaced from the ends. The flow occluding point is located between the enlarged tubing portion and the container, and the tubing portion is initially of lay-flat type prior to passing blood through it.

Following this occlusion step, one draws more blood through the needle to enter the enlarged tubing portion. One then occludes the flexible tubing at a point between the enlarged tubing portion and the needle, prior to withdrawing the needle from the vein of the blood donor.

Either or both of the steps of occluding the flexible tubing may be simply performed by means of a hemostat or any desired clamp for the flexible tubing, a large variety of tubing clamps being commercially available. Additionally and preferably, one may provide a conventional transverse heat seal across the tubing at the site of the first occluding step recited above, using for example a radio frequency sealer. Typically, this takes place at a time subsequent to the first occluding step, to provide a permanent, transverse seal.

Preferably, the transversely enlarged tubing portion of the lay-flat type comprises a pair of flexible, thermoplastic sheets sealed together to define the transversely enlarged tubing portion. The sheets define opposed, open areas between them for access, with portions of the flexible tubing other than the transversely enlarged tubing portion being sealed within the open areas to form a leakproof, flexible tubing system. Thus, typically, the donor tubing described above provides a first, cylindrical tube section that communicates between the donor needle and one of the open areas of the transversely enlarged tubing portion. Another segment of flexible, cylindrical tubing then communicates between the other opposed, open area of the transversely enlarged tubing portion at one end and communicates with the blood storage container at the other end.

Because the transversely enlarged tubing portion is made of a pair of sealed, flexible, thermoplastic sheets, it may be of the lay-flat type as described herein, being capable of swelling up in the manner of a balloon when filled with blood. Typically, the seal that defines the transversely enlarged tubing portion may be an RF seal, while the thermoplastic sheet and cylindrical tubing may be made of polyvinylchloride, in accordance with conventional technology. Typically, the transversely enlarged tubing portion may inflate to hold about 20–40 ml. of blood, typically about 28–30 ml.

Also, it is preferred for the transversely enlarged tubing portion to be free of any tubular member within said tubing portion. A related patent, Wilson et al, U.S. Pat. No. 3,654,924, shows a blood collection assembly in which an auxiliary sample pouch with a pass-through tube is provided. The pass-through tube is of the same diameter as the remaining tubing of the assembly, and is frangible within the pouch for opening so that the tubing can be placed in communication with the pouch to fill it with auxiliary blood, if desired.

However, by way of disadvantage, the device of the Wilson et al patent requires manipulating of the sample pouch to break the frangible tube near the donor's arm with the needle installed in the vein. This is deemed to be undesirable since a slip of the hand or the like can knock the needle and damage the vein. Also, a problem may arise from particulate materials which are generated by the breaking of the frangible connection, so that undesirable particles from the connector pass into the blood.

By the method of this application, an increased amount of blood for sampling may be added to a blood collection system, where the blood for sampling remains free from any added anticoagulant/nutrient found in the container. This is so even if there is no valve or other means for preventing the anticoagulant/nutrient from passing into the donor tube during storage of the blood container prior to use, because the blood storage container is initially filled by blood passing through the donor tube and its transversely enlarged portion, causing any anticoagulant/nutrient to be washed with the blood back into the storage container. Thus, the blood for sampling is the last amount of blood collected, and remains free of anticoagulant/nutrient after the first flow occluding step recited above.

In the normal collection of the blood, the lay-flat, transversely enlarged tubing portion normally does not completely fill with blood, but rather the blood forms a stream that passes therethrough from end to end, with the transversely enlarged tubing staying in a relatively lay-flat configuration. Then, upon the first occluding step described above, the further collection of blood causes the lay-flat tubing to inflate more, depending upon the amount of blood that is collected.

DESCRIPTION OF SPECIFIC EMBODIMENTS

Figure 1:
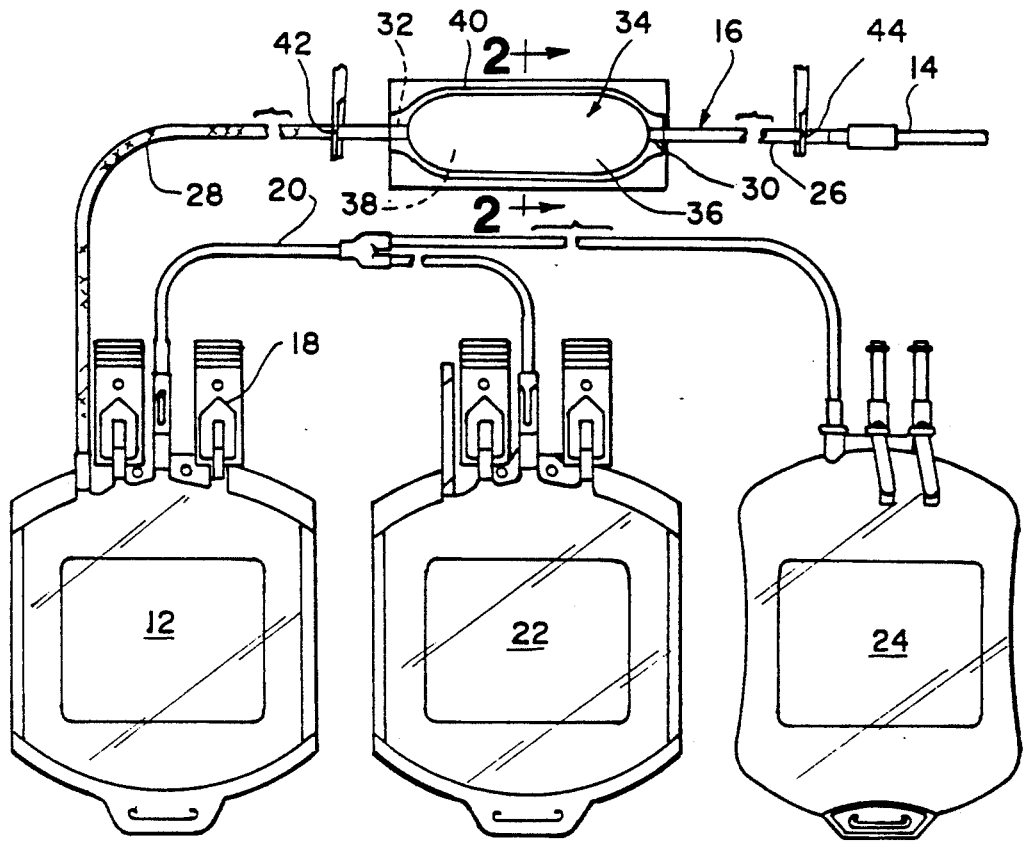
FIG. 1 is a plan view of a multiple blood bag collection system in accordance with this invention.

Referring to the drawings, there is shown a multiple bag blood collection system 10 which may be of conventional, commercial design except as otherwise specifically disclosed herein, and which may be used to perform the method of this application.

Blood system 10 comprises a first bag 12 for receiving and storing donated blood. As is generally conventional, a donor needle 14 (shown with its protective sheath in place) is connected to donor tubing 16 which, in turn, communicates with first bag 12. As is conventional, bag 12 comprises a pair of peripherally heat sealed sheets with bag 12 carrying conventional access ports 18 and transfer tubing 20 of conventional design, which transfer tubing is branched to connect with transfer bags 22, 24, which may also be conventional. Transfer bags 22, 24 are typically for the collection respectively of plasma and platelets after the blood donation is complete and the system has been centrifuged.

As is further conventional, bag 12 contains a small amount of an anticoagulant/nutrient solution, typically CPD, ACD, or ADSOL (T.M.) preservative solution for blood cells.

Figure 2:
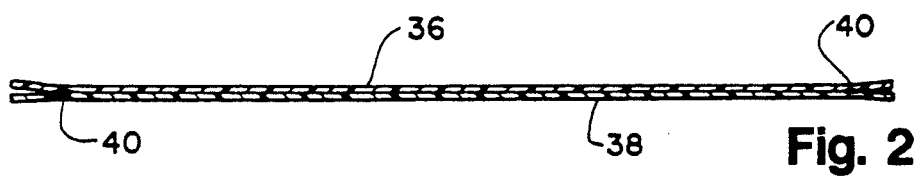
FIG. 2 is a cross-section taken along line 2—2 of FIG. 1 showing the lay-flat configuration.

In the specific embodiment shown, donor tubing 16 comprises a pair of flexible, cylindrical tubes 26, 28 which respectively connect to and are sealed into opposed open ports 30, 32 of flexible, transversely enlarged tubing portion 34, which is positioned at a location on donor tubing 16 spaced from the ends thereof. Enlarged tubing portion 34 is shown to comprise a pair of flexible, thermoplastic sheets 36, 38, which are sealed together by a heat seal line 40 to define the transversely enlarged tubing portion between them. Thus, because of this construction, tubing portion 34 is of the lay-flat configuration in its initial form, as shown in FIG. 2, being specifically shown to be of the general shape of a flat-sided oval in its lay-flat configuration as shown in FIG. 1.

Accordingly, when it is desired to obtain additional blood for sampling during a blood donation, needle 14 is positioned in the vein in the patient, and blood is allowed to flow through donor tubing 16 to fill donor bag 12. During this time, blood passes through tubing portion 34, but tends not to be retained there, so that tubing portion 34 tends to stay in a configuration which is not much expanded from its initial, lay-flat configuration.

Then, if it is desired to terminate the blood collection without collecting an increased amount of blood, but only that amount of blood that resides in donor tubing 16, the blood collection process can be terminated at this stage in a conventional manner.

Figure 3:
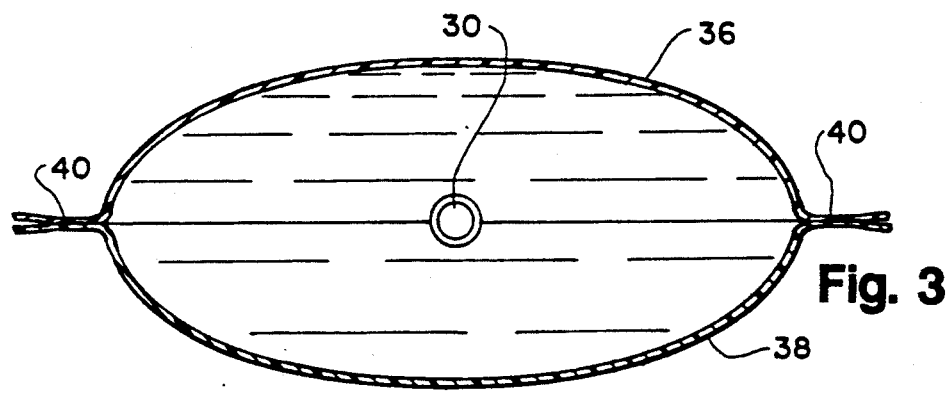
FIG. 3 is a cross-section similar to FIG. 2 showing the same transversely enlarged tubing portion in its configuration when filled with blood.

However, if it is desired to collect extra blood for the added analytical techniques that are currently available, one clamps donor tube 16 at point 42 between enlarged tubing portion 34 and bag 12, making use of a hemostat or any other desired clamp. Blood is allowed to continue to flow through needle 14 and donor tube section 26, to fill enlarged tubular portion 34, which expands outwardly like an inflated balloon to typically hold about 28–30 ml. of blood, as shown in FIG. 3.

Following this, one clamps donor tubing section 28 at a point 44 adjacent the end of needle 14, making use of another hemostat or clamp, and needle 14 is withdrawn from the vein in a conventional manner.

Following this, needle 14 may be penetrated into a blood sample vial of conventional design, and the clamping at point 44 released so that the vial may receive blood from the filled tubular section 34. Several vials may receive blood in this manner, which blood is reliably free of any liquid diluents from the donor bag 12 such as ADSOL or any other anticoagulant/nutrient solutions.

After blood collection, the donor tubing 16 may be transversely heat sealed in conventional manner to assure the sterility of the collected blood, and also if desired to maintain segments of blood for sampling in donor tubing portion 28, and as is conventional. Indicia may be placed on the donor tubing 16 to identify the various transversely sealed segments and to correlate them with the rest of the collected blood, as is conventional.

Thus, increased amounts of blood for sampling and analysis may be provided by a blood collection system in accordance with this invention, without the risk of dilution of sample as described above, and without the need of collecting the increased amount of blood in those circumstances when such increased amount is not necessary. In that case where one wishes to not collect an increased amount of blood, any residual blood remaining in enlarged tubing portion 34 may be sent downstream to the donor bag 12 at the termination of blood collection. This can be accomplished by squeezing the blood from enlarged chamber 34 to tube 28, or simply by elevating enlarged chamber 34 substantially over blood bag 12. Then, one may clamp at site 42 with a hemostat. Alternatively, if it is not desired to send such a residue of blood to donor bag 12, it may be disposed of along with the remainder of the set.

It can be seen that enlarged tubing portion 34 is free of any tubular member within such tubing portion, which member would increase the cost of the blood collection unit, and which also has the disadvantages previously described.

The above has been offered for illustrative purposes only, and is not intended to limit the scope of the invention of this application, which is as defined in the claims below.

That which is claimed is:

1. In the method of connecting into the vein of a blood donor a donor needle which communicates with a flexible, collapsible blood collection container through flexible tubing connected at respective ends to said needle and container, and drawing blood through said needle and tubing into said container, the improvement comprising, in combination:

after drawing a desired amount of blood into the container, occluding flow through said flexible tubing at a point adjacent a flexible, transversely enlarged lay flat, in line tubing portion positioned at a location on the tubing spaced from the ends, said flow occluding point being located between said enlarged tubing portion and said container, said tubing portion being initially of lay-flat type prior to passing blood through it;

drawing more blood through said needle to enter said enlarged tubing portion; and then occluding said flexible tubing at a point between said enlarged tubing portion and said needle prior to withdrawing said needle from the vein of the blood donor.

2. The method of claim 1 in which said transversely enlarged tubing portion is free of any inner tubular member within said tubing portion.

3. The method of claim 1 in which said transversely enlarged, lay-flat tubing portion comprises a pair of flexible, thermoplastic sheets sealed together to define said transversely enlarged tubing portion, said sheets defining a pair of opposed, open areas between them, and portions of said flexible tubing other than said transversely enlarged tubing portion being sealed within said open areas to form a leakproof, flexible tubing.

4. The method of claim 1 in which said, transversely enlarged, lay-flat tubing portion is of the shape of a flat-sided oval in the lay-flat configuration.

5. The method of claim 1 in which said transversely enlarged tubing portion can hold 20 to 40 ml. of blood.

6. In the method of connecting into the vein of a blood donor, a donor needle which communicates with a flexible, blood collection container through flexible tubing connected at respective ends to said needle and container, and drawing blood through said needle and tubing into said container, the improvement comprising, in combination:

after drawing a desired amount of blood into the container, clamping said flexible tubing at a point adjacent a flexible, transversely enlarged tubing portion positioned at a position on the tube spaced from the ends, said clamping point being located between the enlarged tubing portion and the container, the tubing portion being initially of lay-flat type prior to blood passing through it, said transversely enlarged, lay-flat tubing portion comprising a pair of thermoplastic sheets sealed together to define said transversely enlarged tubing portion, said sheets defining a pair of opposed, open areas between them, and portions of flexible tubing other than said transversely enlarged tubing portion being sealed within said open areas to form a leakproof, flexible tubing;

drawing more blood through said needle to enter said enlarged tubing portion; and then clamping said flexible tubing at a point between said enlarged tubing portion and said needle prior to withdrawing said needle from the vein of said blood donor.

7. The method of claim 6 in which said transversely enlarged tubing portion can hold 20-40 ml. of blood.

8. The method of claim 7 in which said transversely enlarged tubing portion is of the shape of a flat-sided oval in a lay-flat configuration.

9. The method of claim 8 in which the transversely enlarged tubing portion is free of any inner tubular member within said tubing portion.

10. The method of claim 1 in which flow through said flexible tubing is occluded by inward collapsing of the walls of said tubing.

* * * * *